(12) United States Patent
Zelechonok

(10) Patent No.: US 8,702,130 B1
(45) Date of Patent: Apr. 22, 2014

(54) FITTING WITH IMPROVED TUBE CLAMPING CAPABILITY

(75) Inventor: Yury Zelechonok, Northbrook, IL (US)

(73) Assignee: SIELC Technologies Corporation, Prospect Heights, IL (US)

( * ) Notice: Subject to any disclaimer, the term of this patent is extended or adjusted under 35 U.S.C. 154(b) by 1 day.

(21) Appl. No.: 13/464,076

(22) Filed: May 4, 2012

(51) Int. Cl.
*F16L 17/00* (2006.01)

(52) U.S. Cl.
USPC .......................................... 285/342; 285/357

(58) Field of Classification Search
USPC ........................... 285/342, 257, 324, 357, 356
See application file for complete search history.

(56) References Cited

U.S. PATENT DOCUMENTS

| | | | | |
|---|---|---|---|---|
| 900,974 A * | 10/1908 | Andrews | ....................... | 285/243 |
| 996,114 A | 6/1911 | Muller | | |
| 1,370,289 A * | 3/1921 | Crippen | ....................... | 285/250 |
| 1,468,707 A * | 9/1923 | Johnston | ....................... | 285/243 |
| 1,801,403 A * | 4/1931 | White | ....................... | 285/116 |
| 1,872,536 A * | 8/1932 | Weatherhead, Jr. | ......... | 285/148.6 |
| 2,127,611 A * | 8/1938 | Mueller | ....................... | 285/342 |
| 2,219,218 A | 10/1940 | Berger et al. | | |
| 2,383,692 A | 8/1945 | Smith | | |
| 2,388,179 A | 10/1945 | Prowd | | |
| 2,420,617 A * | 5/1947 | Paquin | ....................... | 285/243 |
| 2,446,599 A * | 8/1948 | Knaggs | ....................... | 285/243 |
| 2,462,323 A * | 2/1949 | Hurst | ....................... | 285/250 |
| 2,475,741 A * | 7/1949 | Goeller | ....................... | 403/308 |
| 2,523,874 A * | 9/1950 | Moore | ....................... | 285/250 |
| 2,832,598 A * | 4/1958 | Strub | ....................... | 273/129 R |
| 3,668,612 A * | 6/1972 | Nepovim | ....................... | 439/584 |
| 4,281,679 A * | 8/1981 | Stearns | ....................... | 137/515.5 |
| 4,328,979 A | 5/1982 | Stoll | | |
| 4,441,837 A | 4/1984 | Mastroni | | |
| 4,544,186 A * | 10/1985 | Proni | ....................... | 285/243 |
| 4,552,387 A | 11/1985 | Schmidt | | |
| 4,666,190 A * | 5/1987 | Yamabe et al. | ................. | 285/93 |
| 4,666,192 A * | 5/1987 | Zamora | ....................... | 285/322 |
| 4,998,831 A | 3/1991 | Proni | | |
| 5,503,437 A | 4/1996 | Cronley | | |
| 5,744,100 A * | 4/1998 | Krstanovic | ....................... | 422/537 |
| 6,926,313 B1 * | 8/2005 | Renzi | ....................... | 285/353 |
| 7,909,367 B2 | 3/2011 | Plant et al. | | |
| 2010/0156089 A1 | 6/2010 | Zelechonok et al. | | |
| 2011/0025047 A1 | 2/2011 | Zelechonok et al. | | |
| 2011/0089683 A1 * | 4/2011 | Maunder | ....................... | 285/257 |
| 2011/0298210 A1 * | 12/2011 | Hochgraeber et al. | ........ | 285/357 |

* cited by examiner

*Primary Examiner* — Aaron Dunwoody
(74) *Attorney, Agent, or Firm* — John C. Shepard

(57) ABSTRACT

A fitting for holding a tube in fluid communication with a cooperating component having a port with an internal thread of preselected pitch includes a coupling body with a longitudinal bore for receiving the tube, a grippable portion, and radially displaceable, tube clamping fingers separated by longitudinal slots. An external thread is defined on the surface of the fingers and is engageable with the internal thread of the port. The external thread has a pitch diameter similar to the pitch diameter of the internal thread and a pitch dissimilar to the pitch of the internal thread. Rotation of the fitting relative to the component to engage the threads effects relative axial movement thereof and radial displacement of the fingers into clamping engagement with the tube to hold it within the fitting. A sealing end ferrule may be included on the forward end of the coupling body.

17 Claims, 5 Drawing Sheets

FITTING WITH IMPROVED TUBE CLAMPING CAPABILITY

BACKGROUND OF THE INVENTION

1. Technical Field

The present invention relates to a fitting for coupling a tube to a receiving component and, more particularly, to a fitting wherein rotation effects axial engagement to the component and radial clamping of the tube therein.

2. Background Art

High pressure liquid chromatography (HPLC) systems typically operate at pressures of 5,000 PSI and higher. To withstand these pressures, capillary tubing that connects the various system components is formed from an advanced polymer or plastic or stainless steel. End fittings or couplings are used to tightly clamp, seal and connect the tubing to the HPLC components.

More specifically, end fittings typically have a tubular construction with a through bore sized to receive the capillary tube. The forward end of the fitting typically has an external thread for mechanically connecting the fitting with a cooperating threaded tap of a HPLC component. A separate or integrated tubular ferrule is provided on the fitting forward end.

The fitting has a rearward radially enlarged region suited for finger gripping that allows a user to rotate the fitting without tools with sufficient torque to tighten or loosen it relative to the HPLC component.

When the fitting is tightened into a HPLC component, the forward end ferrule is compressed between the fitting, capillary tube and HPLC component, creating a somewhat small annular region of pressurized ferrule that seals and mechanically clamps the tube and fitting together.

The forces between the ferrule and tube must be substantial in this region as they essentially form the only means axially holding the tube and fitting together. It is not uncommon to have clamping forces on the compressed ferrule that deform the underlying annular region of the tube.

Nonetheless, as this compressed annular ferrule/tube region is small, the generated axial holding force they provide frequently is inadequate at high pressure such that axial tube blowout from the fitting can occur and possibly result in system failure.

BRIEF SUMMARY OF THE INVENTION

The present invention is directed to overcoming one or more of the problems as set forth above.

The primary object of the present invention is to provide a fitting for holding and sealing a tube, such as a capillary, relative to a cooperating component, such as an HPLC component, utilizing flexible finger-like grippers that can be biased against the tube with a clamping force sufficient to firmly hold the tube relative to the fitting and minimize connection failure in high-pressure applications.

It is a further object to provide a fitting that can be used with existing components without modification.

In an exemplary embodiment of the present invention, a fitting for holding a tube in fluid communication with a port of a cooperating component includes a coupling body with a tube receiving bore and fingers having radially displaceable free ends and an external thread engageable with an internal thread defined in the component port. The pitch diameter of the external thread of the fitting is substantially similar to the pitch diameter of the internal thread of the component port so that they may be engaged. The pitch of the external thread is dissimilar to the pitch of the internal thread so that relative axial movement engaging the threads causes the external thread to travel up the internal thread flank surface to effect inward radial movement of the fingers into clamping engagement with the tube.

It is a feature of the present invention that the user by rotating the fitting effects clamping of the tube within the fitting without additional manipulation thereby increasing the likelihood that the user fully secures the tube within the fitting.

In one aspect of the present invention, the finger thread has a pitch greater than the receiving port pitch.

In another aspect of the present invention, the fingers define circumferentially spaced slots extending longitudinally from the coupling body forward end rearwardly and radially between the tube receiving bore and its outer edge.

In another aspect of the present invention, the sides of the coupling body are truncated at the slot outer edge so that the external thread is comprised of segments between the slots, thereby increasing the flexibility of the fingers and further enabling the finger thread to move radially on the port thread flank surface.

In another aspect of the present invention, the coupling body includes a grippable portion inboard of the fitting rearward end facilitating rotation of the fitting relative to the receiving component.

In yet another aspect of the present invention, the fitting holds an aligned end ferrule that provides a seal between the cooperating component, the fitting and the tube, and also acts as a clamp between the fitting and the tube passing therethrough.

A further feature of the present invention is that while the fitting can apply sufficient force to clamp the tube within the fitting, the fitting may be easily removed, releasing the tube clamping forces, allowing tube removal, and tube insertion or adjustment relative to the fitting.

BRIEF DESCRIPTION OF THE SEVERAL VIEWS OF THE DRAWINGS

The details of construction and operation of the invention are more fully described with reference to the accompanying drawings which form a part hereof and in which like reference numerals refer to like parts throughout.

In the drawings.

Figure 1:
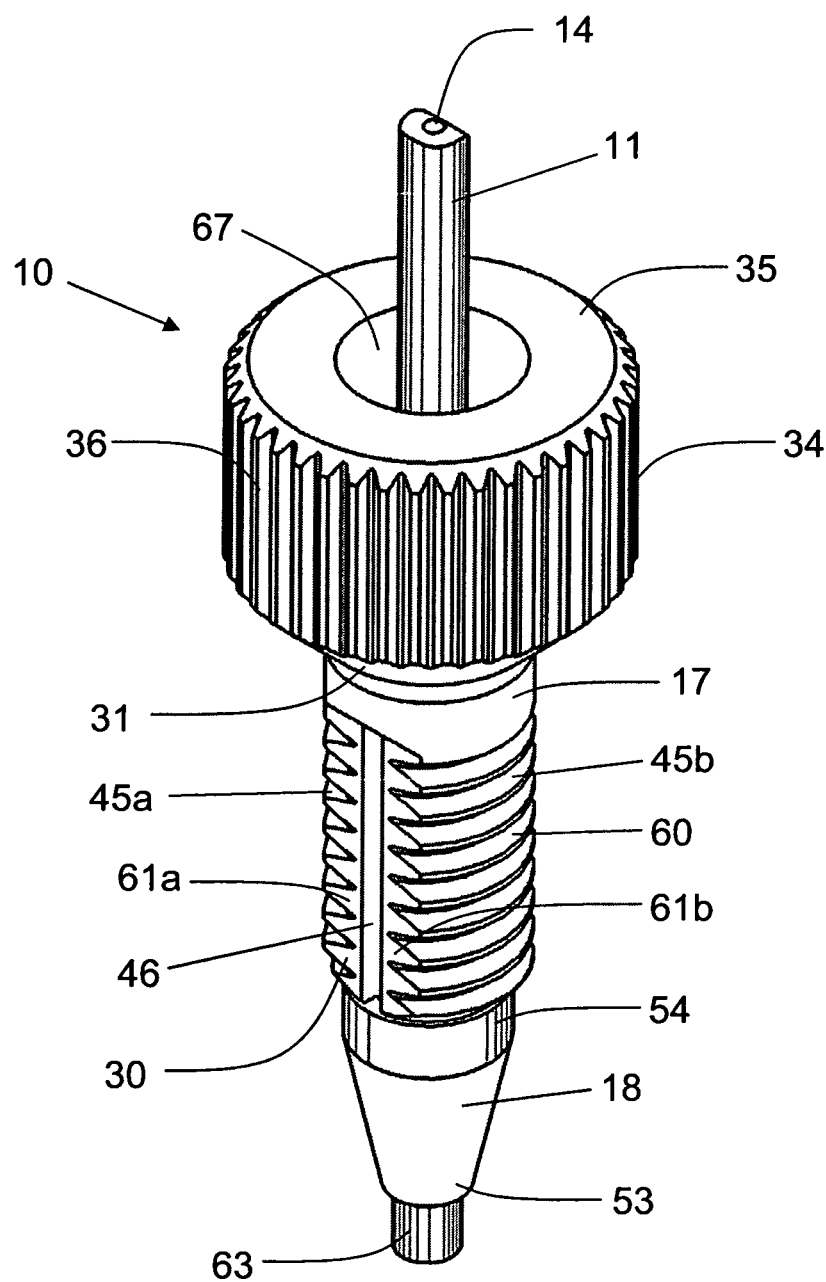
FIG. 1 is a vertical perspective view of a fitting embodying the principles of the invention.
Figure 2:
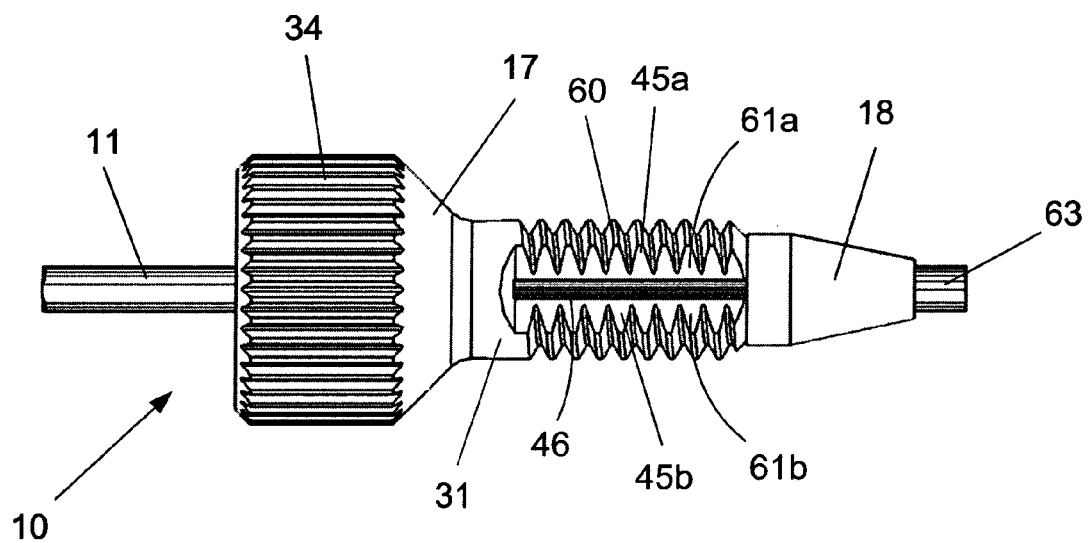
FIG. 2 is a side elevational view of the fitting of FIG. 1 showing the slot and flat surfaces on one side thereof.
Figure 3:
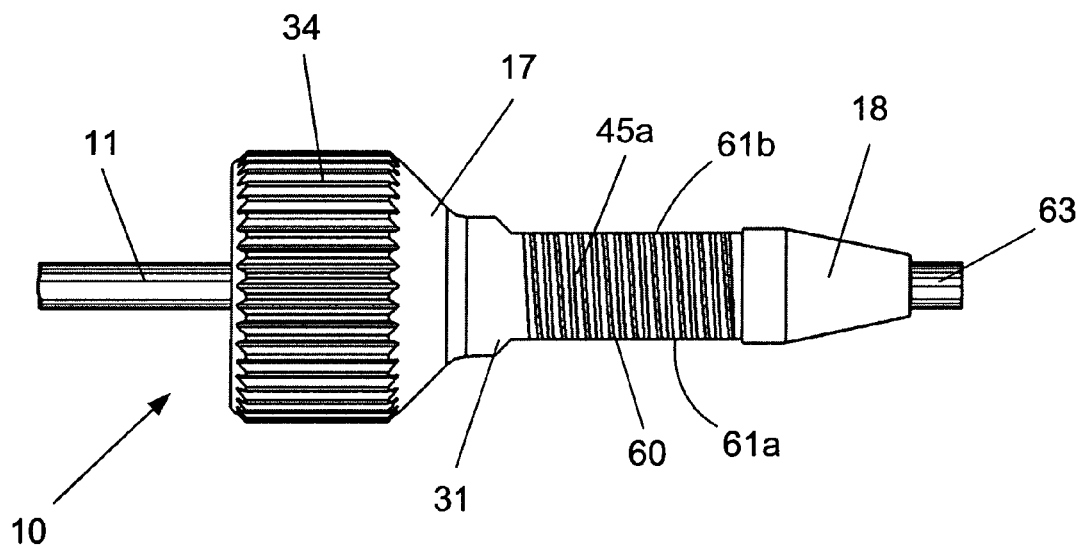
FIG. 3 is a top elevational view of the fitting of FIG. 1 showing the external thread form on one side thereof.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood.

DETAILED DESCRIPTION OF THE PREFERRED EMBODIMENTS

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated. To illustrate the function of the invention, its application within an HPLC system is described, but it should be fully understood that the present invention is not limited to HPLC use only.

Figure 4:
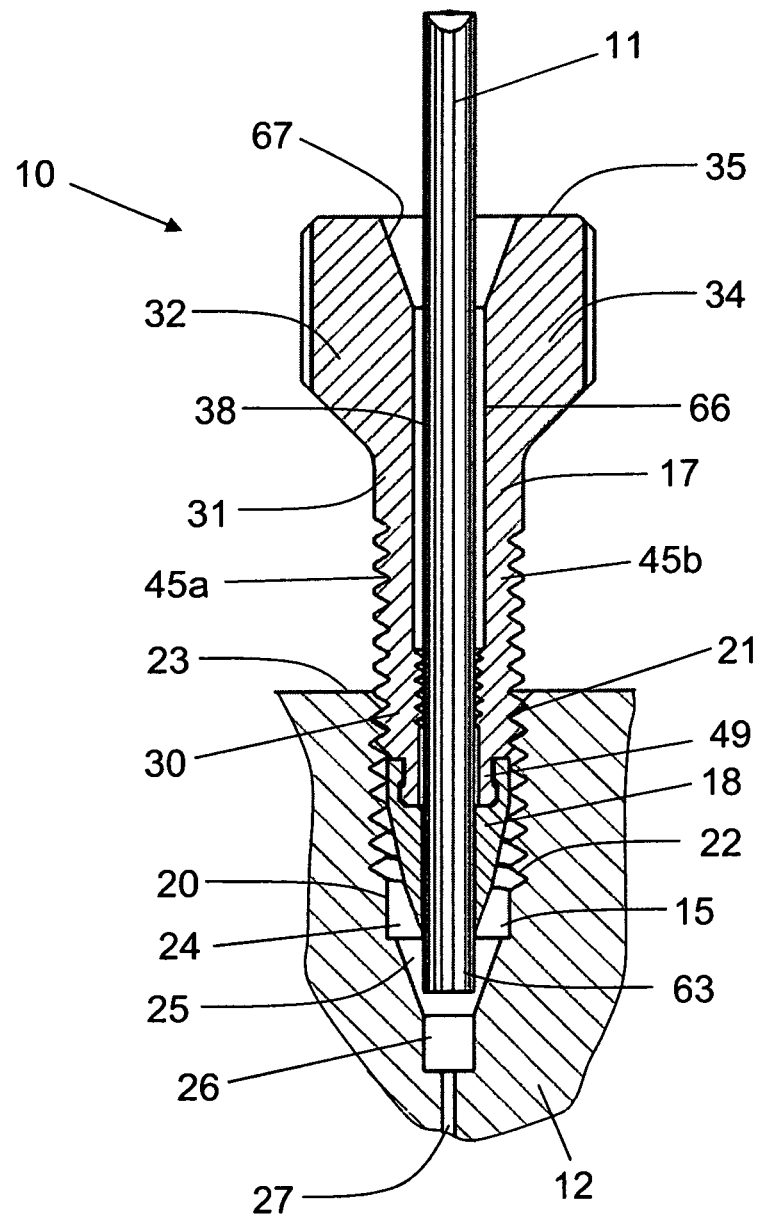
FIG. 4 is a vertical cross-sectional view of the fitting of FIG. 1 showing the fitting fingers partially threaded into the port of a receiving component.

Referring to the drawings in greater detail, and more particularly to FIGS. 1 and 4, a threaded fitting, generally designated 10, for securely attaching a tube 11 to a cooperating receiving component, partially shown and designated 12, enabling fluid communication between the tube passage 14 and the component is seen to include an elongate coupling body 17 and a generally frustoconical tube ferrule 18 disposed at its inner or forward end 19. The component may be part of a HPLC system, such as a pump, valve, guard column, separating column, detector, and other HPLC parts (not shown), which are connected together by various tube segments.

Typically, the component 12 has a threaded port 15 adapted to receive the fitting 11. The port 15 includes a bore 20 having an outer portion 21 with an internal thread 22 extending longitudinally inwardly of the component outer surface 23, an intermediate unthreaded portion 24 with a frustoconical section 25 and a tube receiving, narrow inward section 26, and a relatively small flow passage 27 extending therefrom for fluid transmission.

The coupling body 17, which may be formed from any suitable metal, has a forward portion 30, an intermediate portion 31, and a rearward portion 32 including a large diameter grippable segment 34 inboard of its outer or rearward end face 35. The cylindrical grippable segment 34 is provided with circumferentially spaced longitudinal ridges, collectively designated 36, to facilitate rotation of the fitting 10 about a longitudinal center axis. The ridges 36 may also take the form of corrugations, knurls, or the like to provide an unsmooth or roughened surface that a user may manually grasp. The grippable segment 34 may also be appropriately configured to receive a cooperating tool, such as a wrench (not shown), that enables the user to mechanically rotate the fitting 10. The coupling body 17 and end ferrule 18 are somewhat tubular and have respective longitudinal through bores 38 and 39 aligned on the fitting center axis and sized to have the tube 11 axially positionable therein.

The coupling body forward portion 30 includes a pair of circumferentially spaced, diametrically opposed, cantilevered fingers 45a and 45b anchored to the intermediate portion 31 and extending forwardly. As seen, the forward portion 30 is bifurcated by diametrically opposed, circumferentially spaced slots 46 that extend forwardly to the finger free ends and radially from the bore 38 through the fingers 45a and 45b to an outer edge. At the free ends of the fingers 45a and 45b are forward end segments 49 defining steps 50 with inboard mounting grooves 51.

The compressible end ferrule 18 is formed from polyetheretherketone (PEEK) and has a small diameter outboard end 53 and a large diameter inboard end 54. An opening 55 with an internal flange 56 extends axially at the inboard end enabling the ferrule 18 to be press fit over the steps 50 on the body projecting end segments 49 with the flange 56 locking into the mounting grooves 51.

An external thread 60 is defined on the partial cylindrical outer surface of the fingers 45a and 45b generally between the projecting end segment 49 and the intermediate portion 31. Flat side surfaces 61a and 61b are formed on either side of the slots 46 at their outer edge and lie generally in a plane perpendicular to the plane of the slots that passes radially inward of the imaginary cylinder defining the root bottom of the external thread thereby truncating the sides of the fingers 45a and 45b adjacent the slot outer edge and decreasing the circumferential extent of the thread 60. As seen, the coupling body 17 has full height between threads along one cross-section with the side surfaces 61a and 61b defining a smaller width without threads along a transverse cross-section. The slots 46 and side surfaces 61 cut the external thread 60 into a series of circumferential external thread segments each subtending an angle between 60° and 120° and being generally aligned end-to-end to form the external thread 60. By decreasing the amount of material forming the fingers 45a and 45b, the fingers are rendered more flexible and the thread area engaging the internal thread 22 of the receiving component 12 is decreased.

When the fitting 10 is rotated axially relative to the receiving component 12, the coupling body external thread 60 is engaged with the receiving component internal thread 22 moving the fitting 10 axially into the component port 15 locking the parts together. The forward end 63 of the tube 11 extends beyond the forward end 53 of the ferrule 18 into the inward section 26 closely positioning the tube passage 14 with the component passage 27. The ferrule 18 is pressed radially against by the surface of the component frustoconical section 25 effecting a seal between the component 12 and ferrule 18 and a seal between the ferrule 18 and the tube 11. Radial pressure of the ferrule bore wall acting on the tube exterior wall provides a first tube clamping means frictionally holding the tube 11 within the receiving component 12.

The coupling body bore 38 has a tube gripping segment including a series of internal, arcuately formed, teeth 65 inboard of the projecting segment 49, an intermediate segment 66 diametrically larger than the tube 11, and a funneling conical segment 67 inboard of its diametric end face 35 that facilitates placement of the tube 11 within the bore 38. When the finger free ends are not flexed radially inward, there is sufficient clearance within the coupling body 17 to allow the tube 11 to be inserted freely through or removed from the respective bores 38 and 39. When the fingers 45a and 45b are flexed radially inward by means described hereafter, the gripping teeth 65 which concentrically overlie the tube 11 will mechanically engage the tube exterior and stably hold the tube 11 providing a second tube clamping means. It is understood that the internal gripping segment may take alternative forms, such as knurls, an abrasive or roughened surface, to provide an unsmooth gripping surface, or may be left relatively smooth to hold the tube through friction.

Flexure of the fingers 45 is accomplished by appropriately configuring the internal thread 22 within the component bore 20 and the cooperating external thread 60 on the coupling body 17. For HPLC applications, the fitting and component threads typically have a nominal size of 10-32, i.e., a basic pitch diameter of size 10, or about 0.17 inch, and 32 thread forms or helix turns per inch with the angle between adjacent flank faces of the thread being 60°. To ensure that the mating threads 22 and 60 assemble without interference and do not bind given typical tolerances, the pitch diameter of the external thread 60, although substantially similar, is often selected so that it is slightly less than the pitch diameter of the mating internal thread 22. The crest and root of the thread may be truncated or rounded. Consequently, a gap exists radially and longitudinally between the opposing thread flank faces 70 and 71 with the threads 22 and 60 overlapping in a radial direction by the depth of thread engagement. The resulting backlash or loose clearance fit allows a limited amount of relative axial and radial movement between parts enabling a user to assemble parts more facilely.

In the prior art, mating parts typically have the same pitch, i.e., the same distance between thread centers. As used herein, the definition of the term "pitch" is the distance from the center of one thread form to the center of the next thread form. Pitch is not the number of turns per inch, which is the actually the reciprocal of pitch. The external thread 60 of the fitting disclosed and described herein has a slightly greater pitch, i.e., more spacing or distance between thread centers. Herein, the external thread 60 has 31 turns per inch, so that it has a nominal size of 10-31.

As may be ascertained from FIG. 4, when the fitting 10 is initially inserted into the component bore 20, the threads 22 and 60 will mate smoothly with the external thread form loosely occupying the recesses defined between the internal thread form.

Figure 5:
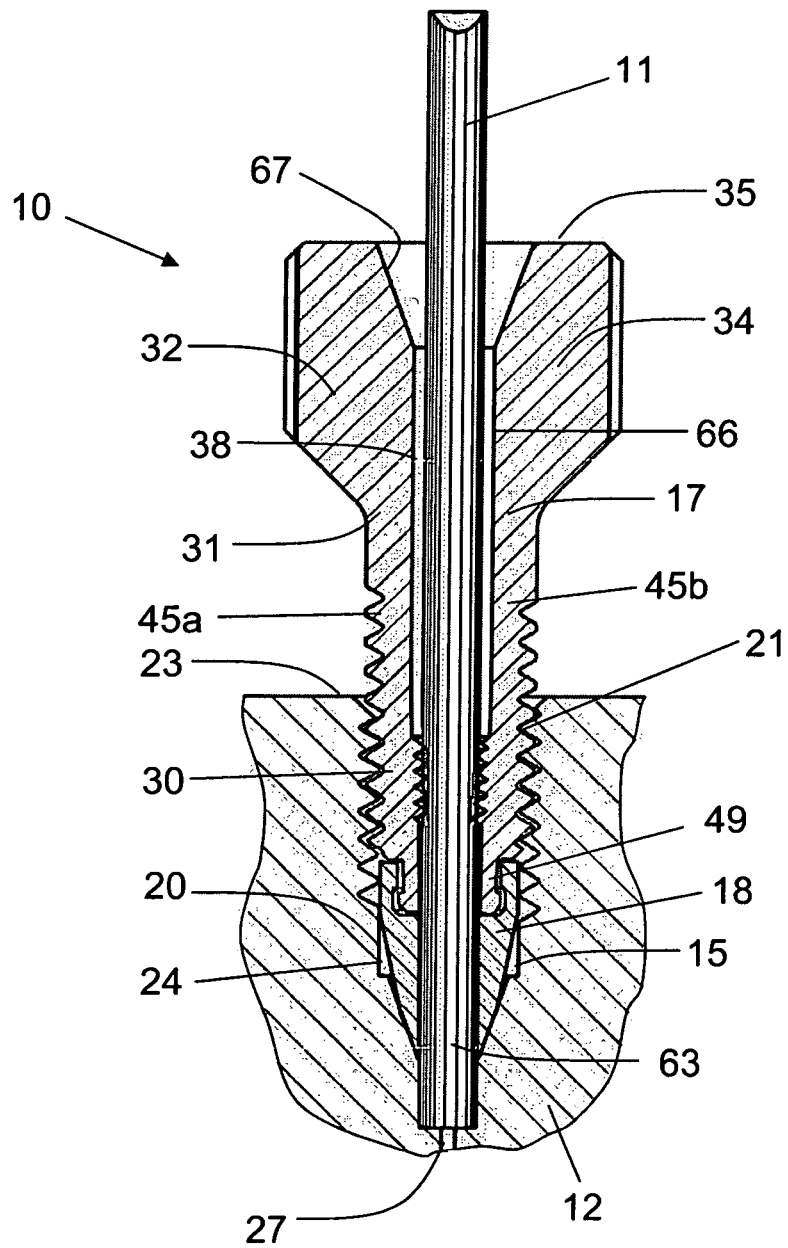
FIG. 5 is a vertical cross-sectional view of the fitting of FIG. 1 similar to FIG. 4, but showing the fitting fingers fully inserted into the receiving port.
Figure 6:
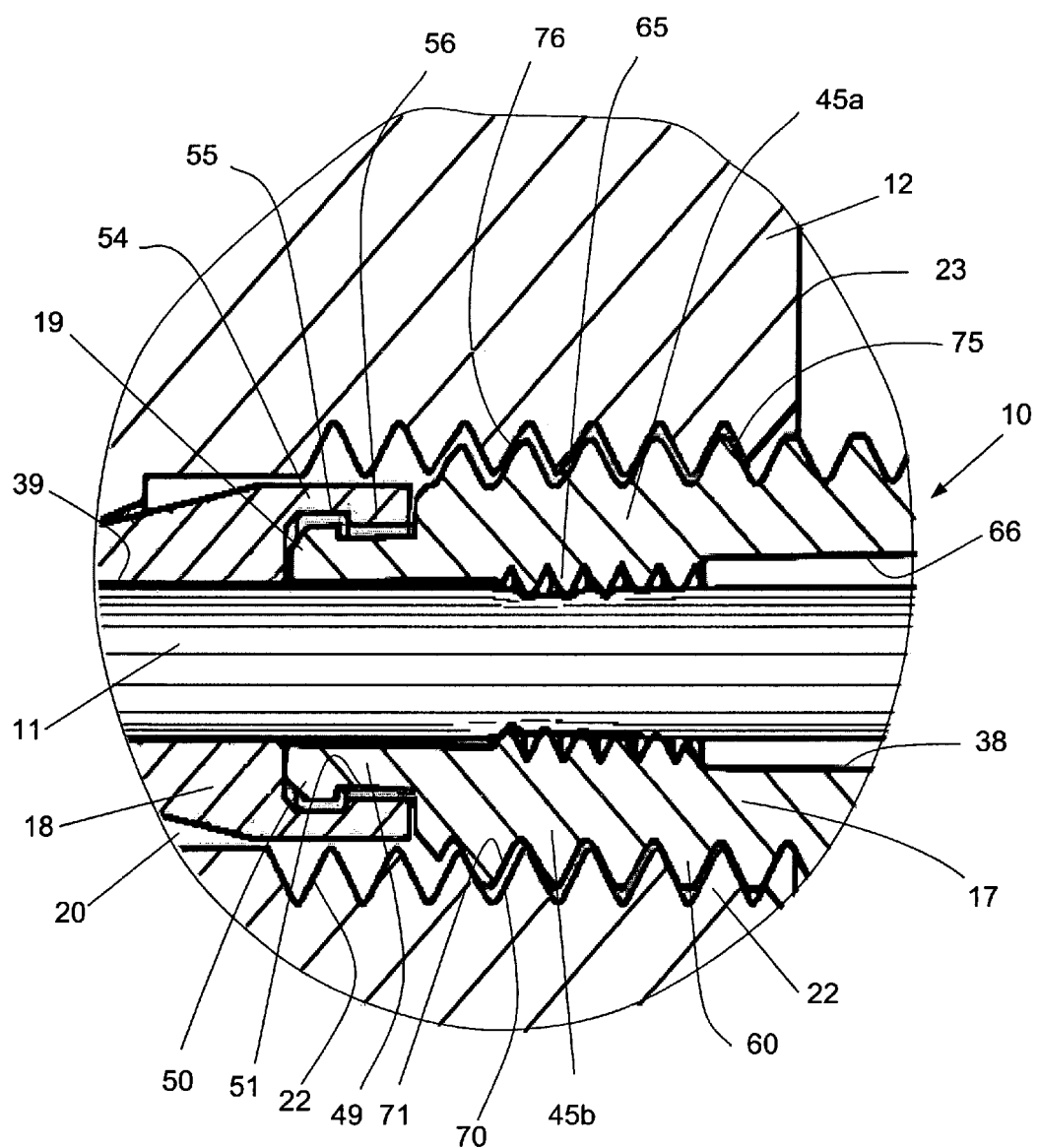
FIG. 6 is an enlarged, partial, cross-sectional view of the fitting of FIG. 5 rotated 90° showing the displacement of the external thread of the fitting finger free ends radially inward from the internal thread of the receiving port.

As shown in FIGS. 5 and 6, because of the difference in pitch, when the fitting 10 is fully threaded into the component bore 20, the rearward external thread form occupies the back portion of the internal thread recess as shown at 75 in FIG. 6 and the forwardly facing flank of the forward external thread form will be driven up the rearwardly facing flank of the internal thread 22 flexing the forward ends of the fingers 45a and 45b radially inward as shown at 76 in FIG. 6. In the exaggerated position shown in FIG. 6, the free end of the top finger 45a is bent downwardly and the free end of the bottom finger 45b is bent upwardly, both into mechanical contact with the tube 11. When the cantilevered fingers 45a and 45b are so flexed, the gripping teeth 65 clamp onto the external wall of the tube 11 to hold it against relative axial movement.

With a single operation, namely, threading the fitting 10 into the component 12 by rotation of the fitting 10, the first and second tube clamping means tightly engage the tube 11 increasing radial force against the tube 11 to prevent it from being forced axially from the fitting.

Since each segment of the external thread 60 only extends around the fingers 45a and 45b between adjacent side flat side surfaces 61a and 61b, which is only a fraction of the pitch circumference, only thread portions at opposite sides of the fitting 10 spaced from the slots 46 engage the component internal thread 22.

While only three full turns of engaged thread are typically required to effectively lock threaded parts axially, additional turns as shown in FIGS. 5 and 6 can be achieved. With the clearances and tolerances of common thread forms, any variation increasing the coupling external thread pitch to about 105 percent of the internal thread pitch can be advantageously employed. The amount of pitch variation is selected so that when the fitting 10 is seated, the desired flex is obtained without deforming or stripping of the threads. A variation of about 2 to 4 percent is preferred for HPLC connections. It is also possible that the fitting thread have a pitch less than that of the internal thread. The diameter of the threaded coupling body 17 between the flat side surfaces is approximately 75 percent of the outside diameter between the thread ridges. In a coupling with a thread size of 10-31, the slot width between the fingers 45a and 45b is about 0.01 to 0.03 inch, or about 5 to 20 percent of the coupling body diameter across the external threads. Changing the width of the slots 46 or adjusting the side surfaces 61a and 61b radially inward or outward so that there is less or more finger material will alter the stiffness of the fingers 45a and 45b and the engageable surface area of the thread 60.

It is understood that while the fitting 10 illustrated herein has two fingers, additional slots may be utilized to define additional tube surrounding fingers, albeit narrower.

INDUSTRIAL APPLICABILITY

It should be apparent the fitting described herein is a simple, functional unit that is effective and inexpensively manufactured and is easy to properly use.

It is understood that the fitting herein is advantageously employed within the HPLC arts as a retrofit with existing components and equipment, but may be advantageously used in other arts as well.

Other aspects, objects and advantages of this invention can be obtained from a study of the drawings, the disclosure, and the appended claims.

It should be understood that the terms "top," "bottom," "forward," "rearward," "first," "second," "upper," "lower," "height," "width," "length," "end," "side," and similar terms as used herein, have reference only to the structure shown in the drawings and are utilized only to facilitate describing the invention. The terms and expressions employed herein have been used as terms of description and not of limitation.

From the foregoing, it will be observed that numerous variations and modifications may be effected without departing from the spirit and scope of the invention. It will also be observed that the various elements of the invention may be in any number of combinations, and that all of the combinations are not enumerated here. It will be understood that no limitation with respect to the specific apparatus illustrated herein is intended or should be inferred. While specific embodiments of the invention have been disclosed, one of ordinary skill in the art will recognize that one can modify the materials, dimensions and particulars of the embodiments without straying from the inventive concept.

What is claimed is:

1. A fitting for holding a tube in fluid communication with a cooperating component having a port with an internal thread defining an internal thread pitch, comprising:

a coupling body having forward and rearward ends and a longitudinal bore extending between said ends along a center axis, said tube being axially positionable within said bore;

said body having a grippable portion forward of said body rearward end for rotating said body about said axis;

said body having circumferentially spaced fingers radially outward of said bore with anchored ends rearwardly and free ends forwardly, said fingers having an internal surface engageable with an external surface of the tube when the tube is positioned in said bore;

an external thread defined on the external surface of said fingers engageable with the internal thread, said external thread having a pitch diameter substantially similar to the internal thread to engage therewith and a pitch dissimilar to the internal thread pitch; and, whereby insertion of the finger free ends into the port and rotation of the fitting relative to the cooperating component engages said threads to effect relative axial movement and whereby the pitch difference upon axial movement effects movement of the finger free ends radially inward with the finger internal surface engaging the tube external surface to hold the tube within the fitting.

2. The fitting of claim 1 wherein the pitch of the external thread is greater than the pitch of the internal thread.

3. The fitting of claim 2 wherein the pitch of the external thread is less than 105 percent of the pitch of the internal thread.

4. The fitting of claim 3 wherein the pitch of the external thread is more than 102 percent and less than 104 percent of the pitch of the internal thread.

5. The fitting of claim 4 wherein the nominal size of the internal thread is 10-32 and the nominal size of the external thread is 10-31.

6. The fitting of claim 1 wherein said fingers define circumferentially spaced slots, each slot extending forwardly of said grippable portion to said forward end and radially from said body bore through said fingers to an outer edge.

7. The fitting of claim 6 wherein said fingers include side surfaces on either side of said slots at said outer edge lying in a plane generally perpendicular to said slots and truncating said fingers adjacent said outer edge, said external thread having segments extending generally circumferentially from one side surface to an adjacent side surface on each finger.

8. The fitting of claim 6 wherein the external thread comprises a series of spaced segments generally aligned end-to-end with adjacent aligned segments disposed on different fingers.

9. The fitting of claim 8 wherein said fingers include side surfaces on either side of said slots at said outer edge lying in a plane generally perpendicular to said slots and truncating said fingers adjacent said outer edge, said external thread having segments extending generally circumferentially from one side surface to an adjacent side surface on each finger.

10. The fitting of claim 8 wherein each thread segment extends around the fitting body between 60° and 120°.

11. The fitting of claim 1 further including an annular ferrule axially aligned on the forward end of said coupling body and fittable over the tube confinable between the tube and the receiving component for producing an annular pressure tight seal between the tube and the receiving component.

12. The fitting of claim 1 wherein said finger internal surface is unsmooth enabling said fingers to clamp the tube more effectively.

13. The fitting of claim 1 wherein said grippable portion is unsmooth enabling a user to grasp and rotate the fitting more easily.

14. A fitting for holding a tube in fluid communication with a cooperating component having a port with an internal thread defining an internal thread pitch, comprising:

a coupling body having forward and rearward ends and a longitudinal bore extending between said ends along a center axis, the tube being axially positionable within said bore;

said body having a grippable portion forward of said body rearward end for rotating said body about said axis;

said body having circumferentially spaced fingers radially outward of said bore with anchored ends rearwardly and free ends forwardly, said fingers having an internal surface engageable with an external surface of the tube when the tube is positioned in said bore, said fingers defining circumferentially spaced slots, each slot extending forwardly of said grippable portion to said forward end and radially from said body bore through said fingers to an outer edge;

an annular ferrule axially aligned on the forward end of said coupling be and fittable over the tube confinable between the tube and the receiving component for producing an annular pressure tight seal between the tube and the receiving component;

an external thread defined on the external surface of said fingers engageable with the internal thread, said external thread having a pitch diameter substantially similar to the internal thread to engage therewith and a pitch greater than the internal thread pitch; and, said fingers including side surfaces on either side of said slots at said outer edge lying in a plane generally perpendicular to said slots and truncating said fingers adjacent said outer edge, said external thread having segments extending generally circumferentially from one side surface to an adjacent side surface on each finger; and, whereby insertion of the finger free ends into the port and rotation of the fitting relative to the cooperating component engages said threads to effect relative axial movement and whereby the pitch difference upon axial movement effects movement of the finger free ends radially inward with the finger internal surface engaging the tube external surface to hold the tube within the fitting.

15. The fitting of claim 12 wherein the pitch of the external thread is more than 102 percent and less than 104 percent of the internal thread.

16. The fitting of claim 1 wherein said finger internal surface is unsmooth enabling said fingers to clamp the tube more effectively.

17. The fitting of claim 1 wherein said grippable portion is unsmooth enabling a user to grasp and rotate the fitting more easily.

* * * * *